US006613345B2

(12) United States Patent
Boucher, Jr.

(10) Patent No.: US 6,613,345 B2
(45) Date of Patent: *Sep. 2, 2003

(54) CONJUGATES OF SODIUM CHANNEL BLOCKERS AND METHODS OF USING THE SAME

(75) Inventor: Richard C. Boucher, Jr., Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/121,917

(22) Filed: Apr. 12, 2002

(65) Prior Publication Data

US 2002/0158255 A1 Oct. 31, 2002

Related U.S. Application Data

(62) Division of application No. 09/618,978, filed on Jul. 19, 2000, now Pat. No. 6,475,509.
(60) Provisional application No. 60/144,479, filed on Jul. 19, 1999.

(51) Int. Cl.$^7$ .................. A61F 13/00; A01N 43/04; A01N 43/60; A61K 31/70; A61K 31/495
(52) U.S. Cl. .................. 424/434; 514/46; 514/255
(58) Field of Search .................. 424/434; 514/255, 514/46

(56) References Cited

U.S. PATENT DOCUMENTS

| 3,313,813 A | 4/1967 | Cragoe, Jr. .................. 260/250 |
| 5,837,861 A | 11/1998 | Pendergast et al. ......... 536/25.6 |
| 6,264,975 B1 * | 7/2001 | Boucher, Jr. .................. 424/434 |

FOREIGN PATENT DOCUMENTS

| WO | WO 94/08593 | 4/1994 | .......... A61K/31/70 |
| WO | WO 96/18385 | 6/1996 | .......... A61K/9/12 |
| WO | WO 96/40059 | 12/1996 | .......... A61K/9/12 |
| WO | WO 00/23023 | 4/2000 | .......... A61F/13/00 |

OTHER PUBLICATIONS

International Search Report, Nov. 20, 2000, Application No. PCT/US00/19775.

* cited by examiner

Primary Examiner—Jezia Riley
(74) Attorney, Agent, or Firm—Myers Bigel Sibley & Sajovec

(57) ABSTRACT

Compounds of the general formula $P_1$-L-$P_2$; wherein "$P_1$" is a pyrazinoylguanidine sodium channel blocker, "L" is a linking group, and "$P_2$" is either (i) a pyrazinoylguanidine sodium channel blocker or (ii) a P2Y$_2$ receptor agonist, are disclosed. Pharmaceutical formulations containing the same and methods of use thereof to hydrate mucosal surfaces such as airway mucosal surfaces are also disclosed.

20 Claims, 2 Drawing Sheets

(1 of 2 Drawing Sheet(s) Filed in Color)

CONJUGATES OF SODIUM CHANNEL BLOCKERS AND METHODS OF USING THE SAME

RELATED APPLICATIONS

This application is a divisional of co-pending U.S. application Ser. No. 09/618,978, filed Jul. 19, 2000, now U.S. Pat. No. 6,475,509 which claims the benefit of U.S. Provisional Application No. 60/144,479, filed Jul. 19, 1999, the disclosure of which is incorporated herein by reference in its entirety.

STATEMENT OF FEDERAL SUPPORT

This invention was made with Government support under Grant No. HL34322 from the National Institutes of Health. The United States government has certain rights in this invention.

FIELD OF THE INVENTION

The present invention relates to conjugates of sodium channel blockers, and particularly covalent conjugates comprising a pyrazinoylguanidine sodium channel blocker and another compound such as another pyrazinoylguanidine sodium channel blocker or a $P2Y_2$ receptor agonist.

BACKGROUND OF THE INVENTION

U.S. Pat. No. 4,501,729 to Boucher describes the use of respirable or non-respirable amiloride to hydrate airway mucous secretions, and U.S. Pat. No. 5,656,256 to Boucher and Stutts describes the use of respirable or non-respirable benzamil and phenamil to hydrate lung mucus secretions. U.S. Pat. No. 5,789,391 to Jacobus describes methods of treating sinusitis by administering uridine triphosphates (UTP) and related compounds such as $P^1,P^4$-di(uridine-5' tetraphosphate ($U_2P_4$) in order to promote drainage of congested fluid in the sinuses.

U.S. Pat. No. 5,292,498 to Boucher describes nucleotides, particularly $P2Y_2$ receptor agonists, that can be used to hydrate airway mucus secretions. Dinucleotides that can be used to hydrate airway mucus secretions are described in U.S. Pat. No. 5,635,160 to Stutts et al.. Additional compounds that are $P2Y_2$ receptor ligands and can be used to hydrate airway mucus secretions are disclosed in W. Pendergast et al., U.S. Pat. No. 5,837,861, along with U.S. Pat. Nos. 5,763,447 to Jacobus and Leighton, and 5,789,391 to Jacobus et al.

SUMMARY OF THE INVENTION

A first aspect of the present invention is a compound (hereinafter also referred to as an "active compound" or "active agent") of the general formula $P_1$-L-$P_2$; wherein "$P_1$" is a pyrazinoylguanidine sodium channel blocker, "L" is a linking group, and "$P_2$" is either (i) a pyrazinoylguanidine sodium channel blocker or (ii) a $P2Y_2$ receptor agonist. An advantage of compounds of the present invention is that they are substantially non-absorbable, or absorption-retardant or exhibit delayed absorption on mucosal (e.g., airway, gastrointestinal) surfaces, thereby contributing to a prolonged mode of action and fewer systemic side effects.

A second aspect of the present invention is a composition comprising an active compound as defined above in an effective therapeutic amount, in a pharmaceutically acceptable carrier.

A third aspect of the present invention is a method of treating a mucosal surface in a subject in need thereof, comprising administering an active compound as described herein in an amount effective to treat the subject. In general, treatment of the subject will mean that the mucosal surface being treated with a compound or composition of the present invention will be hydrated, or that the compound or composition being used will block or otherwise retard the absorption of liquid onto or onto the mucosal surface, or that the mucosal surface will otherwise exhibit an increased volume of liquid on the mucosal surface.

A fourth aspect of the present invention is the use of an active compound as described above for the preparation of a medicament for treating a mucosal surface in a subject in need thereof, as described herein.

The foregoing and other objects and aspects of the present invention are explained in detail in the specification set forth below.

BRIEF DESCRIPTION OF DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
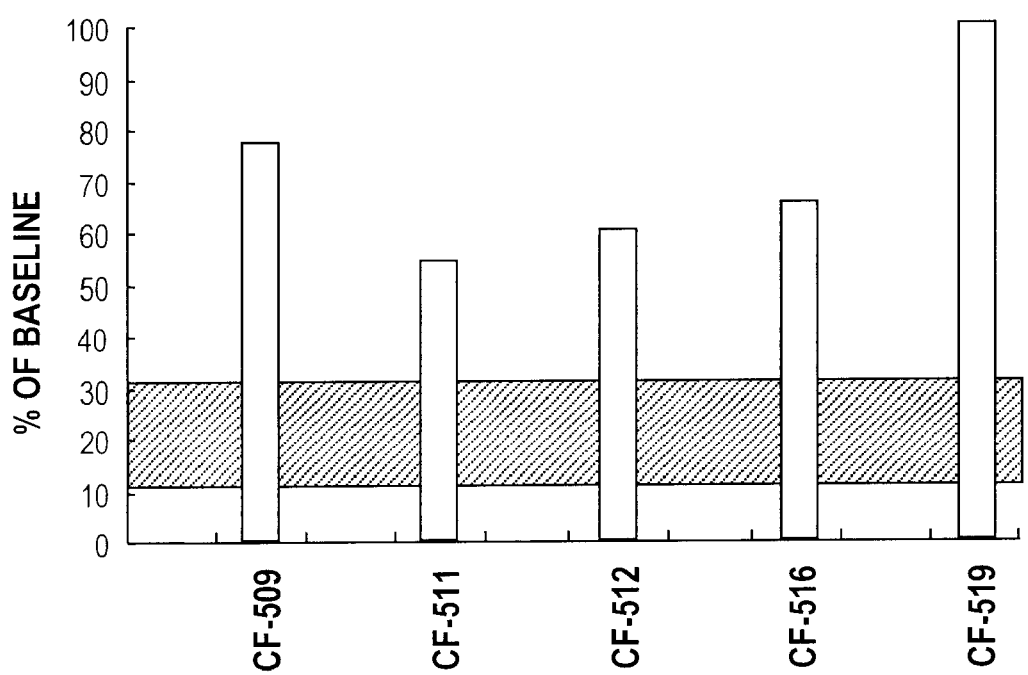
FIG. 1 is a graphical illustration of the effect of apical washout of a compound of the present invention, where wash-out correlates with cellular uptake. A range of reversibilities is shown, with the compound CF-519 being completely reversible.

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The term "alkyl" or "loweralkyl" as used herein refers to C1 to C4, C6 or C8 alkyl, which may be linear or branched and saturated or unsaturated. Cycloalkyl is specified as such herein, and is typically C3, C4 or C5 to C6 or C8 cycloalkyl. Alkenyl or loweralkenyl as used herein likewise refers to C1 to C4 alkenyl, and alkoxy or loweralkoxy as used herein likewise refers to C1 to C4 alkoxy. The term "aryl" as used herein refers to C3 to C10 cyclic aromatic groups such as phenyl, naphthyl, and the like, and includes substituted aryl groups such as tolyl. "Halo" as used herein refers to any halogen group, such as chloro, fluoro, bromo, or iodo. The term "hydroxyalkyl" as used herein refers to C1 to C4 linear or branched hydroxy-substituted alkyl, i.e., —CH$_2$OH, —(CH$_2$)$_2$OH, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc. The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

The present invention is concerned primarily with the treatment of human subjects, but may also be employed for the treatment of other animal subjects (i.e., mammals, avians) for veterinary purposes. Mammals are preferred, with humans being particularly preferred.

The present invention is useful in treating mucosal surfaces in a subject in need of such treatment. "Treatment" includes the hydration of the mucosal surface, or the blocking or retardation of the absorption of liquid onto or into the mucosal surface, or an increase of volume of liquid on the mucosal surface, whether by increasing water or liquid on the mucosal surface, increasing the amount of salt on the surface, or both. In a preferred embodiment, the mucosal surface is an airway surface. The term "airway surface" as used herein refers to airway surfaces below the larynx and in the lungs (e.g., bronchial passages, alveolar passages), as well as air passages in the head, including the sinuses and other nasal airways, and in the region above the larynx. The present invention may also be used to treat mucosal surfaces other than airway surfaces. Such other mucosal surfaces include gastrointestinal surfaces, oral surfaces, genitoureteral surfaces, ocular surfaces or surfaces of the eye, the inner ear, and the middle ear.

Subjects that may be treated by the methods of the present invention include patients afflicted with cystic fibrosis, primary ciliary dyskinesia, chronic bronchitis, chronic obstructive airway disease, artificially ventilated patients, patients with acute pneumonia, etc. Subjects that may be treated by the method of the present invention also include patients being nasally administered supplemental oxygen (which tends to dry the airway surfaces), patients afflicted with an allergic disease or response (e.g., an allergic response to pollen, dust, animal hair or particles, insects or insect particles, etc.) that affect nasal airway surfaces, patients afflicted with an infection caused by a microorganism (e.g., infections caused by such organisms as *Staphylococcis aureus, Haemophilus influenza, Streptococcus pneumoniae, Pseudomonas* spp. etc.) of the nasal airway surfaces, an inflammatory disease that affects nasal airway surfaces, or patients afflicted with sinusitis (wherein the active agent or agents are administered to promote drainage of congested mucous secretions in the sinuses by administering an amount effective to promote drainage of congested fluid in the sinuses).

The compounds of the present invention can be prepared according to methods described herein, as well as in accordance with known techniques or variations thereof which will be apparent to skilled persons in light of the disclosure set forth herein. See, e.g., D. Benos et al., *Proc. Natl. Acad. Sci. USA* 83, 8525 (1986); T. Kleyman et al., *Am. J Physiol*

250 (Cell Physiol. 19): C165–C170 (1986); U.S. Pat. Nos. 3,313,813; 4,501,729; 5,789,391; 5,292,498; 5,635,160; 5,837,861; 5,763,447; and 5,789,391 (the disclosures of all patent references cited herein are incorporated by reference in their entirety).

1. Sodium Channel Blockers.

Any sodium channel blocker (i. e., P$_1$ or P$_2$ in the formula P$_1$-L-P$_2$) can be used to carry out the present invention. Numerous pyrazinoylguanidine sodium channel blockers are disclosed in U.S. Pat. No. 3,313,813 to Cragoe. Amiloride, one particular pyrazinoylguanidine sodium channel blocker, is described at Merck Index Registry No. 426 (12th Ed. 1996). Benzamil (also known as 3,5-diamino-6-chloro-N-(benzylaminoaminomethylene) pyrazinecarboxamide) and phenamil (also known as 3,5-diamino-6-chloro-N-(phenylaminoaminomethylene) pyrazinecarboxamide) are known compounds and are also disclosed in U.S. Pat. No. 3,313,813 to E. Cragoe.

Various additional pyrazinoylguanidine sodium channel blockers that are amiloride analogs are disclosed and described in T. Kleyman and E. Cragoe, *J. Membrane Biol.* 105, 1–21 (1988).

Preferred examples of active compounds that may be used to carry out the present invention are the pyrazinoylguanidine sodium channel blockers disclosed in U.S. Pat. No. 3,313,813, incorporated by reference above. Such compounds have the formula:

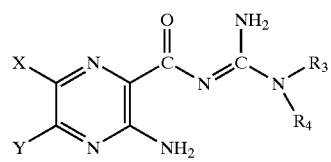

wherein:

X is selected from the group consisting of chloro, bromo, iodo, loweralkyl, lower-cycloalkyl having from 3 to 7 carbons, phenyl, chlorophenyl, bromophenyl, Z-thio and Z-sulfonyl wherein Z is selected from the group consisting of loweralkyl and phenyl-loweralkyl. Preferably, X is chloro.

Y is selected from the group consisting of hydroxyl, mercapto, loweralkyloxy, loweralkylthio, chloro, loweralkyl, lowercycloalkyl having from 3 to 6 carbons, phenyl, amino having the structure:

wherein:

R is selected from the group consisting of hydrogen, amino, amidino, lower-cycloalkyl having 3 to 6 carbon atoms, loweralkyl, hydroxyloweralkyl, haloloweralkyl, lower-(cycloalkylalkyl) having 3 to 6 carbons in the ring, phenyl-loweralkyl, lower-(alkylaminoalkyl), lower-alkenyl, phenyl, halophenyl, and lower-alkylphenyl; alkylphenyl;

R$_1$ is selected from the group consisting of hydrogen, loweralkyl, loweralkenyl, and additionally;

R and $R_1$ can be joined to form a lower alkylene. Preferably, Y is amino.

$R_2$ is selected from the group consisting of hydrogen and loweralkyl. Preferably, R, $R_1$, and $R_2$ are hydrogen.

$R_3$ and R4 are indepenedently selected from the group consisting of hydrogen, loweralkyl, hydroxy-loweralkyl, phenyl-loweralkyl, (halophenyl)-loweralkyl, lower-(alkylphenylalkyl), (loweralkoxyphenyl)-loweralkyl, naphthyl-loweralkyl, (octahydro-1-azocinyl)-loweralkyl, pyridyl-loweralkyl, and loweralkyl radicals linked to produce with the nitrogen atom to which they are attached a 1-pyrrolidinyl, piperidino, morpholino, and a 4-loweralkyl-piperazinyl group, and phenyl. Preferably, $R_3$ is hydrogen, phenyl, or phenylalkyl. Preferably, R4 is hydrogen.

As discussed below, $R_4$ may be replaced with a linking group L.

2. Linking Groups

Any suitable linking group (i.e., "L" in formula $P_1$-L-$P_2$) may be employed. The linking group may be a non-absorbable carrier moiety. The non-absorbable carrier moiety may be a carbohydrate, protein, peptide, polyamine, or water soluble linear polymer. Water soluble linear polymers useful as carrier moieties include polyvinylpyrrolidone, polyethylene glycol, nonylphenol ethoxylates, and polyvinyl alcohol. Carbohydrates useful as carrier moieties include sugars and polysaccharides, such as dextran, lactose, and mannitol. An additional example is agarose. Proteins or peptides useful as carrier moieties include albumin (for example, human serum albumin) and protamine. Polyamnines useful for carrying out the present invention include spermine and spermidine.

The linking groups may be the same as those groups set forth for $R_4$ above, except that they are provided in divalent rather than univalent form. Linking groups may also be heteroatoms, such as —O. Thus the linking group may be an alkylene, alkylenecarbonyl, carbonylalkylene, or a carbonyl group, as follows:

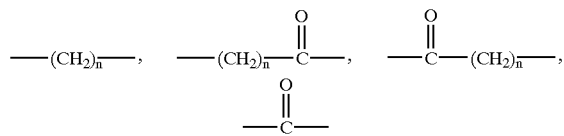

where n is 0 (i.e., a direct covalent linkage) or is from 1 to 6. Such alkylene groups may be saturated or unsaturated, and may be substituted 1, 2, 3, or 4 times with C 1 -C4 alkyl, halo, phenyl, or halo-substituted phenyl. Examples are as follows:

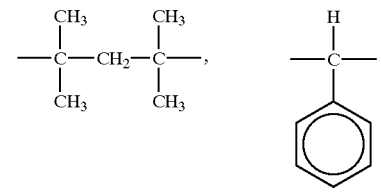

A phenyl or phenylene group, or two or more linked phenylene groups, may be provided as the linking group, which phenylene group may optionally be substituted 1, 2, 3 or four times with a halogen or alkyl group. Examples are as follows:

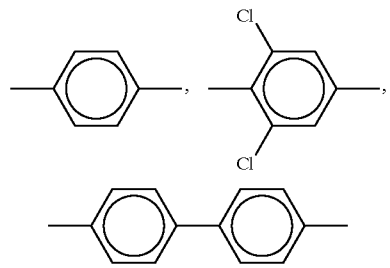

A substituted or unsubstituted phenylene group may be joined at either or both ends with a substituted or unsubstituted alkylene, alkylenecarbonyl, carbonylalkylene, or carbonyl group as described above to provide a linking group. Examples are as follows:

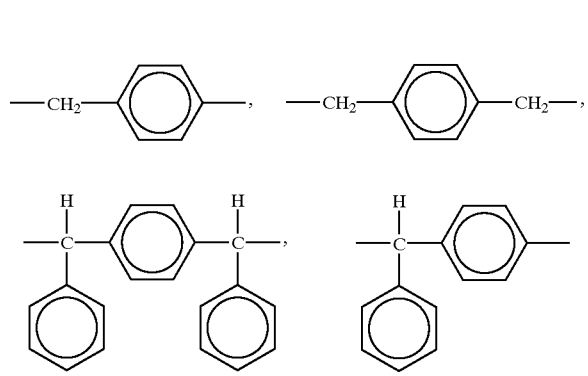

A substituted or unsubstituted alkylene, alkylenecarbonyl, carbonylalkylene, or carbonyl group as described above may joined at either or both ends to a substituted or unsubstituted phenylene group as described above to provide a linking group. Examples are as follows:

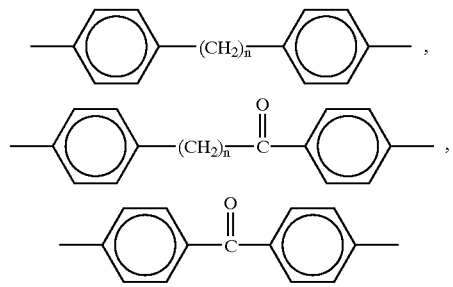

wherein "n" is as defined above. Such compounds may be further substitued at either or both ends by a substituted or unsubstituted alkylene, alkylenecarbonyl, carbonylalkylene, or carbonyl group, as described above, to provide still further linking groups. Examples are as follows:

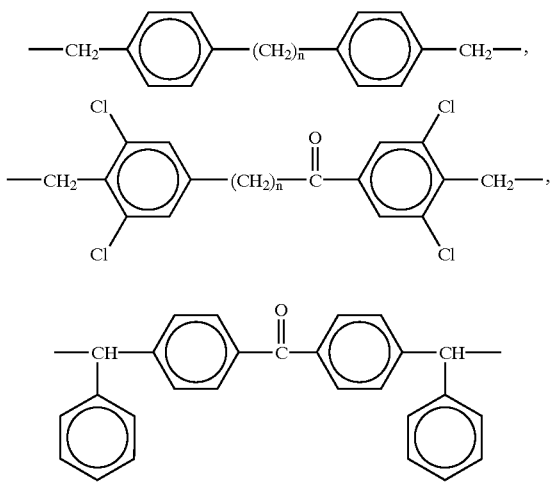

where "n" is as defined above.

3. P2Y₂ Receptor Agonists

As noted above P₂ may also be a P2Y₂ receptor ligand, such as a nucleotide (e.g., ATP, UTP), dinucleotide (described in more detail hereinbelow), or derivative thereof. P2Y₂ receptor ligands that can be used to carry out the present invention include all of the compounds, particularly the nucleotides and dinucleotides that are P2Y2 ligands and are disclosed in W. Pendergast et al., U.S. Pat. No. 5,837,861 (Nov. 17, 1998), along with all the compounds disclosed in U.S. Pat. Nos. 5,763,447 to Jacobus and Leighton, 5,789,391 to Jacobus et al., 5,635,160 to Stutts et al., and 5,292,498 Boucher, the disclosures of all of which are incorporated herein by reference in their entirety.

Examples of such nucleotides are depicted in Formulae I–IV

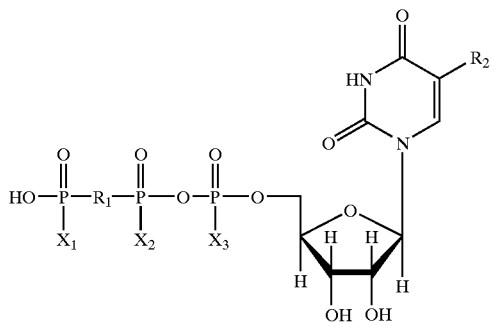

wherein:
$X_1$, $X_2$ and $X_3$ are each independently either O⁻ or S⁻; preferably, $X_2$ and $X_3$ are O⁻;
$R_1$ is O, imido, methylene or dihalomethylene (e.g., dichloromethylene or difluoromethylene); preferably, $R_1$ is oxygen or difluoromethylene;
$R_2$ is H or Br; preferably, $R_2$ is H; particularly preferred compounds of Formula I are uridine 5'-triphosphate (UTP) and iiridine 5'-0-(3-thiotriphosphate) (UTPγS).

A dinucleotide is depicted by the general Formula II:

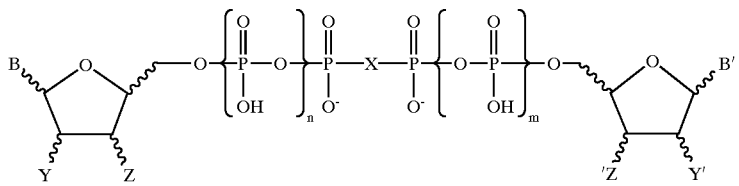

wherein:
X is oxygen, methylene, difluoromethylene, imido;
n=0,1, or 2;
m=0,1, or 2;
n+m=0,1,2,3, or 4; and
B and B' are each independently a purine residue or a pyrimidine residue linked through the 9- or 1-position, respectively;
Z=OH or $N_3$;
Z'=OH or $N_3$;
Y=H or OH;
Y'=H or OH;
provided that when Z is $N_3$, Y is H or when Z' is $N_3$, Y' is H.

The furanose sugar is preferably in the β-configuration.
The furanose sugar is most preferably in the β-D-configuration.
Preferred compounds of Formula II are the compounds of Formula IIa:

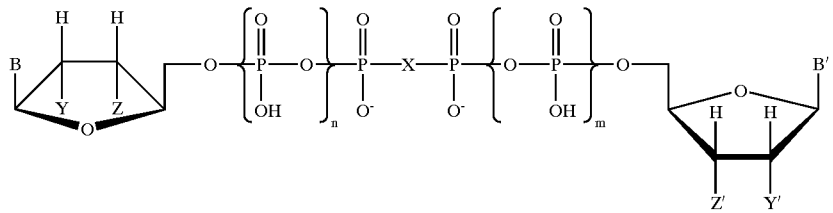

wherein:
  X=O;
  n+m=1 or 2;
  Z, Z', Y, and Y'=OH;
  B and B' are defined in Formulas IIc and IId;
  X=O;
  n+m=3 or 4;
  Z, Z', Y, and Y'=OH;
  B=uracil;
  B' is defined in Formulas IIc and IId; or
  X=O;
  n+m=1 or 2;
  Z, Y, and Y'=OH;
  Z'=H;
  B=uracil;
  B' is defined in Formulas IIc and IId; or
  n+m=0,1, or 2;
  Z and Y=OH;
  Z'=N$_3$;
  Y'=H;
  B=uracil;
  B'=thymine; or
  X=O;
  n+m=0, 1, or 2;
  Z and Z'=N$_3$;
  Y and Y'=H;
  B and B'=thymine; or
  X=CH$_2$, CF$_2$, or NH;
  n and m=1;
  Z, Z', Y, and Y'=OH;
  B and B'are defined in Formulas IIc and IId .
Another preferred group of the compounds of Formula II are the compounds of Formula IIb or the pharmaceutically acceptable salts thereof:

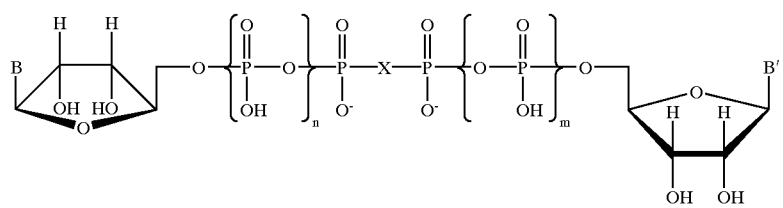

wherein:

X is oxygen, methylene, difluoromethylene, or imido;
n=0 or 1;
m=0 or 1;
n+m =0, 1, or 2; and B and B' are each independently a purine residue, as in Formula IIc, or a pyrimidine residue, as in Formula IId, linked through the 9- or 1- position, respectively. In the instance where B and B' are uracil, attached at N-1 position to the ribosyl moiety, then the total of m+n may equal 3 or 4 when X is oxygen. The ribosyl moieties are in the D-configuration, as shown, but may be L-, or D- and L-. The D-configuration is preferred.

Formula IIc

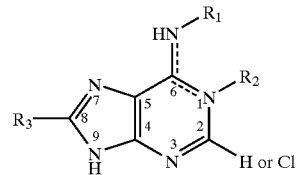

The substituted derivatives of adenine include adenine 1-oxide; 1,N$^6$-(4- or 5-substituted etheno) adenine; 6-substituted adenine; or 8-substituted aminoadenine, where R' of the 6- or 8-HNR' groups are chosen from among: arylalkyl (C$_{1-6}$) groups with the aryl moiety optionally functionalized as described below; alkyl; and alkyl groups with functional groups therein, such as: ([6-aminohexyl] carbamoylmethyl)-, and ω-acylated-aminohydroxy, thiol and carboxy) derivatives where the acyl group is chosen from among, but not limited to, acetyl, trifluroroacetyl, benzoyl, substituted-benzoyl, etc., or the carboxylic moiety is present as its ester or amnide derivative, for example, the ethyl or methyl ester or its methyl, ethyl or benzamido derivative. The ω-amino(hydroxy, thiol) moiety may be alkylated with a C$_{1-4}$ alkyl group.

Likewise, B or B' or both in Formula IIb may be a pyrimidine with the general formula of FIG. IId, linked through the 1 -position:

FIG. IId

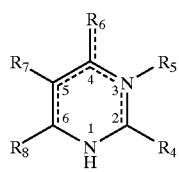

wherein:
  R$_4$ is hydroxy, mercapto, amino, cyano, aralkoxy, C$_{1-6}$ alkoxy, C$_{1-6}$ alkylamino, and dialkylamino, the alkyl groups optionally linked to form a heterocycle;
  R$_5$ is hydrogen, acyl, C$_{1-6}$ alkyl, aroyl, C$_{1-5}$ alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino, or dialkylamino, where the alkyl groups are optionally linked to form a heterocycle or linked to N-3 to form an optionally substituted ring;

$R_7$ is hydrogen, hydroxy, cyano, nitro, alkenyl, with the alkenyl moiety optionally linked through oxygen to form a ring optionally substituted on the carbon adjacent to the oxygen with alkyl or aryl groups, substituted alkynyl or hydrogen where $R_8$ is amino or substituted amino and halogen, alkyl, substituted alkyl, perhalomethyl (e.g., $CF_3$), $C_{2-6}$ alkyl, $C_{2-3}$ alkenyl, or substituted ethenyl (e.g., allylamino, bromvinyl and ethyl propenoate, or propenoic acid), $C_{2-3}$ alkynyl or substituted alkynyl when $R_6$ is other than amino or substituted amino and together $R_5$-$R_6$ may form a 5- or 6-membered saturated-or unsaturated ring bonded through N or O at $R_6$, such a ring may contain substituents that themselves contain functionalities;

$R_8$ is hydrogen, alkoxy, arylalkoxy, alkylthio, arylalkylthio, carboxamidomethyl, carboxymethyl, methoxy, methylthio, phenoxy, or phenylthio.

In the general structure of FIG. IId above, the dotted lines in the 2- to 6—positions are intended to indicate the presence of single or double bonds in these positions; the relative positions of the double or single bonds being determined by whether the $R_4$, $R_6$, and $R_7$ substituents are capable of keto-enol tautomerism.

In the general structures of FIG. IIc and IId above, the acyl groups advantageously comprise alkanoyl or aroyl groups. The alkyl groups advantageously contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above mentioned alkenyl and alkynyl groups advantageously contain 2 to 8 carbon atoms, particularly 2 to 6 carbon atoms, e.g., ethenyl or ethynyl, optionally substituted by one or more appropriate substituents as described below. Appropriate substituents on the above-mentioned alkyl, alkenyl, alkynyl, and aryl groups are advantageously selected from halogen, hydroxy, $C_{1-4}$ alkoxy, $C_{1-4}$ alkyl, $C_{6-12}$ arylalkoxy, carboxy, cyano, nitro, sulfonamido, sulfonate, phosphate, sulfonic, amino, and substituted amino wherein the amino is singly or doubly substituted by a $C_{1-4}$ alkyl, and when doubly substituted, the alkyl groups optionally being linked to form a heterocycle.

For purposes of further clarifying the foregoing descriptions of Formulae IIc and IId, the descriptions can be simplified to the following:

$R_2$ is O or is absent; or $R_1$ and $R_2$ taken together may form optionally substituted 5-membered fused imidazole ring; or $R_1$ of the 6-HN$R_1$ group or $R_3$ of the 8-HN$R_3$ group is chosen from the group consisting of:
(a) arylalkyl ($C_{1-6}$) groups with the aryl moiety optionally substituted,
(b) alkyl,
(c) ([6-aminohexyl]carbamoylmethyl),
(d) ω-amino alkyl ($C_{2-10}$),
(e) ω-hydroxy alkyl ($C_{2-10}$),
(f) ω-thiol alkyl ($C_{2-10}$),
(g) ω-carboxy alkyl ($C_{2-10}$),
(h) the ω-acylated derivatives of (b), (c) or (d) wherein the acyl group is either acetyl, trifluroacetyl, benzoyl, or substituted-benzoyl alkyl($C_{2-10}$), and
(i) ω-carboxy alkyl ($C_{2-10}$) as in (e) above wherein the carboxylic moiety is an ester or an amide;

Formula IId

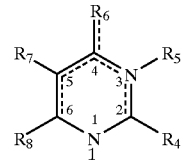

wherein:

$R_4$ is hydroxy, mercapto, amino, cyano, aralkoxy, $C_{1-6}$ alkylthio, $C_{1-6}$ alkoxy, $C_{1-6}$ alkylamino or dialkylamino, wherein the alkyl groups of said dialkylamino are optionally linked to form a heterocycle;

$R_5$ is hydrogen, acyl, $C_{1-6}$ alkyl, aroyl, $C_{1-5}$ alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino or dialkylamino, wherein the alkyl groups of said dialkylamino are optionally linked to form a heterocycle or linked to $N^3$ to form an optionally substituted ring;

$R_5$ - $R_6$ together forms a 5 or 6-membered saturated or unsaturated ring bonded through N or O at $R_6$, wherein said ring is optionally substituted;

$R_7$ is selected from the group consisting of:
(a) hydrogen,
(b) hydroxy,
(c) cyano,
(d) nitro,
(e) alkenyl, wherein the alkenyl moiety is optionally linked through oxygen to form a ring optionally substituted with alkyl or aryl groups on the carbon adjacent to the oxygen,
(f) substituted alkynyl
(g) halogen,
(h) alkyl,
(i) substituted alkyl,
(j) perhalomethyl,
(k) $C_{2-6}$ alkyl,
(l) $C_{2-3}$ alkenyl,
(m) substituted ethenyl,
(n) $C_{2-3}$ alkynyl and
(o) substituted alkynyl when $R_6$ is other than amino or substituted amino;

$R_8$ is selected from the group consisting of:
(a) hydrogen,
(b) alkoxy,
(c) arylalkoxy,
(d) alkylthio,
(e) arylalkylthio,
(f) carboxamidomethyl,
(g) carboxymethyl,
(h) methoxy,
(i) methylthio,
(j) phenoxy and
(k) phenylthio.

CTP and its analogs are depicted by general Formula III:

Formula III

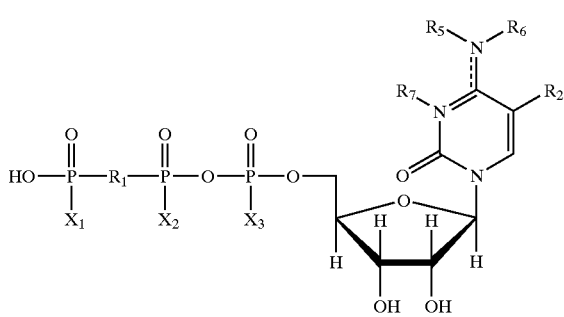

wherein:

$R_1$, $X_1$, $X_2$, and $X_3$ are defined as in Formula I;

$R_5$ and $R_6$ are H while $R_7$ is nothing and there is a double bond between N-3 and C-4 (cytosine), or $R_5$, $R_6$ and $R_7$ taken together are —CH=CH—, forming a ring from N-3 to N-4 with a double bond between N-4 and C-4 (3,$N_4$-ethenocytosine) optionally substituted at the 4- or 5-position of the etheno ring.

ATP and its analogs are depicted by general Formula IV:

Formula IV

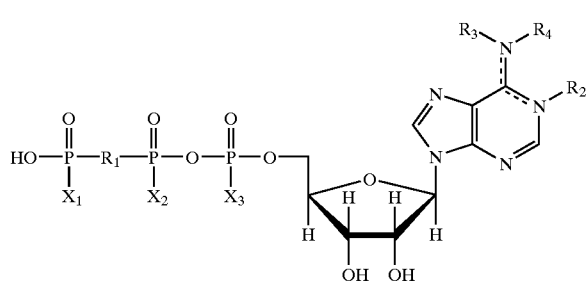

wherein:

$R_1$, $X_1$, $X_2$, and $X_3$ are defined as in Formula I;

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,N6-ethenoadenine).

For simplicity, Formulas I, II, III, and IV herein illustrate the active compounds in the naturally occurring D-configuration, but the present invention also encompasses compounds in the L-configuration, and mixtures of compounds in the D-and L-configurations, unless otherwise specified. The naturally occurring D-configuration is preferred.

Some compounds of Formulas I, II, III, and IV can be made by methods which are well known to those skilled in the art and in accordance with known procedures (Zamecnik, P., et al., *Proc. Natl Acad. Sci. USA* 89:2370–2373 (1992); Ng, K., et al., *Nucleic Acids Res.* 15:3572–3580 (1977); Jacobus, K. M., et al., U.S. Pat. No. 5,789,391 and Pendergast, W., et al., International Patent Application WO98/34942)); some are commercially available, for example, from Sigma Chemical Company, PO Box 14508, St. Louis, Mo. 63178. The synthetic methods of U.S. Pat. No. 5,789,391 and International Patent Application WO98/34942 are incorporated herein by reference in their entirety.

Thus, examples of compounds that can be used to carry out the present invention include compounds of Formula I–IV above, and include compounds having the general formula:

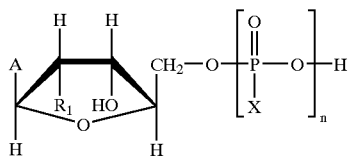

wherein:

X may be O or S;

A is a purine or pyrimidine base (e.g., adenine, guanine, thymine, cytosine, uracil)(each purine or pyrimidine base is preferably joined to the ribose or deoxyribose ring by covalent bond to the 9 nitrogen in the case of purines, or by covalent bond to the 1 nitrogen in the case of pyrimidines);

$R_1$ is H or OH; and n is from 1 to 4 or 6, preferably 2, 3 or 4.

Additional examples of receptor agonists that can be used to carry out the present invention are dinucleotides, including those having the general formula:

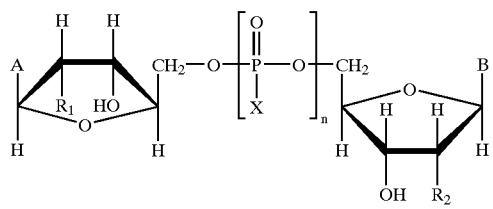

wherein:

A and B are each independently a purine or pyriaidine base (e.g., adenine, guanine, thymine, cytosine, uracil); preferably, A is uracil and B is cytosine;

$R_1$ and $R_2$ are each independently selected from the group consisting of H or OH; and n is from 1 to 6, preferably 3 or 4.

For P2Y$_2$ receptor ligands as described herein, the linking group may be covalently joined to the purine or pyrimidine base, or the corresponding ribose or deoxyribose ring (e.g., of the compounds of Formula I–IV above), or attached to the terminal phosphate moiety of compounds represented by Formulae I, II and IV above, by any suitable means, such as by covalently joining the linking group thereto in any suitable position (e.g., a ring carbon such as the 5 carbon in a pyrirnidine, or the 2, 6 or 8 carbon in a purine), to which linking group the ligand may be covalently attached.

4. Example Conjugate Compounds

Specific examples of active compounds of the present invention, where $P_2$ is a pyrazinoylguanidine sodium channel blocker, include but are not limited to the following:

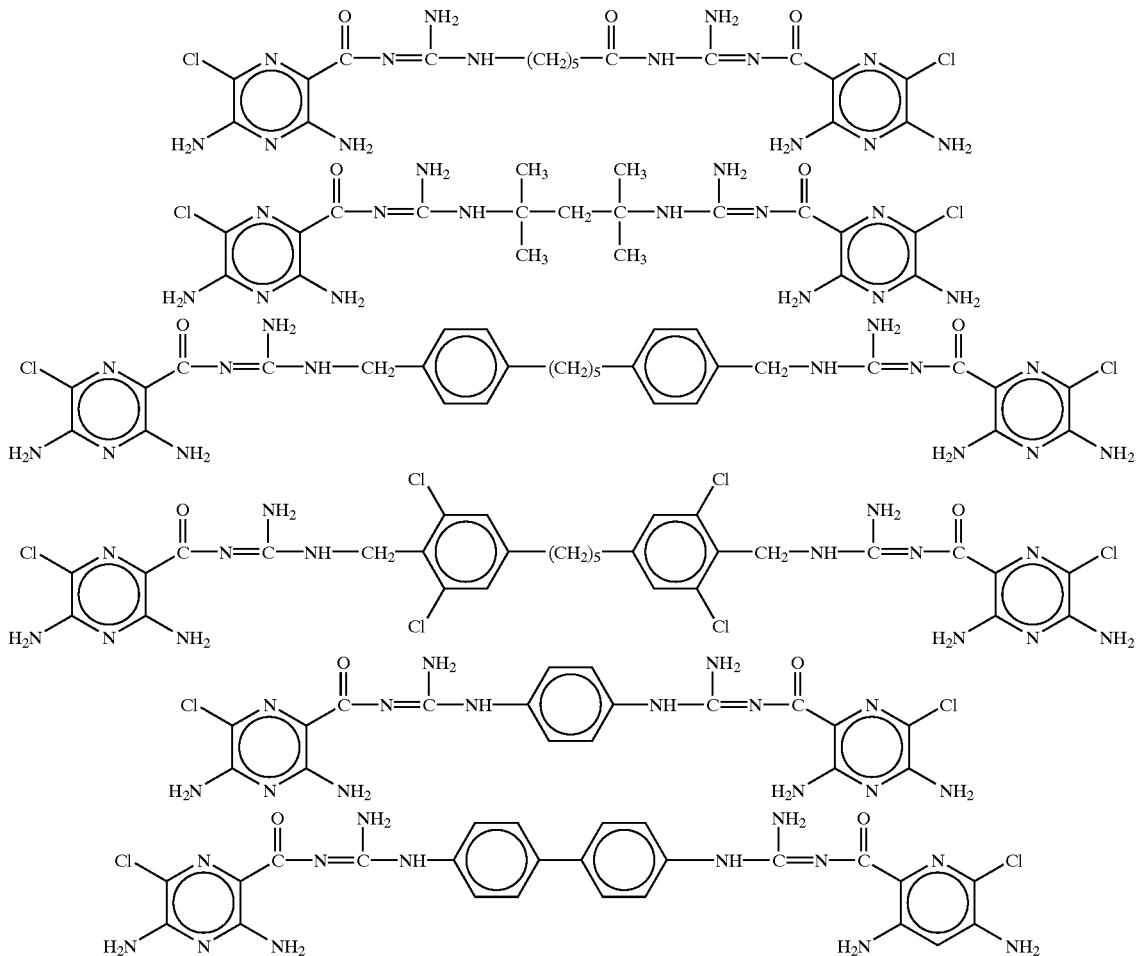

Additional examples of conjugate compounds useful in the present invention include those compounds whose structures are shown in Table 1, below, and in the Examples that follow.

Examples of active compounds of the present invention, where $P_2$ is a P2Y$_2$ receptor ligand, are as follows:

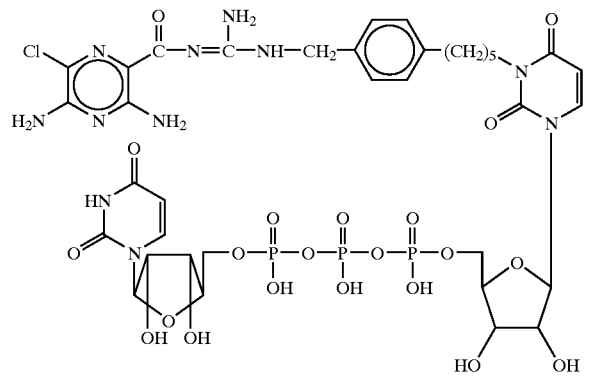

5. Pharmaceutically Acceptable Salts

The term "active agent" as used herein, includes the phar-naceutically acceptable salts of the compound, such as (but not limited to) benzamil hydrochloride or phenamil hydrochloride. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine and iodine.

For nucleotides or dinucleotide active compounds, the compounds may be prepared as an alkali metal salt such as sodium or potassium, an alkaline earth metal salt, or an ammonium and tetraalkyl ammonium salt, $NX_4^+$ (wherein X is a $C_{1-4}$ alkyl group. Pharmaceutically acceptable salts are salts that retain the desired biological activity of the parent compound and do not impart undesired toxicological effects.

Active agents used to prepare compositions for the present invention may alternatively be in the form of a pharmaceutically acceptable free base of active agent. Because the free base of the compound is less soluble than the salt, free base compositions are employed to provide more sustained release of active agent to the lungs. Active agent present in the lungs in particulate form which has not gone into solution is not available to induce a physiological response, but serves as a depot of bioavailable drug which gradually goes into solution.

6. Formulations and Administration

A third aspect of the present invention is a pharmaceutical formulation, comprising an active compound as described above in a pharmaceutically acceptable carrier (e.g, an aqueous carrier solution). In general, the active compound is included in the composition in an amount effective to treat mucosal surfaces, such as inhibit the reabsorption of water by airway surfaces, including nasal airway surfaces.

The active compounds disclosed herein may be administered to mucosal surfaces by any suitable means, including topically, parenterally (e.g., by intraveneous, intramuscular, or intraperitoneal injection), orally, rectally, via inhalation, transdermally, etc. For example, for the treatment of constipation, the active compounds may be administered orally or rectally to the gastrointestinal mucosal surface. The active compound may be combined with a pharmaceutically acceptable carrier in any suitable form, such as sterile physiological saline for an injectable or topical solution, as a droplet, tablet or the like for oral administration, as a suppository for rectal or genito-ureteral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological saline solution or distilled water. For example, the active compounds may be prepared as formulations and administered as described in U.S. Pat. No. 5,789,391 to Jacobus, the disclosure of which is incorporated by reference herein in its entirety.

In one preferred embodiment they are administered by administering an aerosol suspension of respirable or non-respirable particles (preferably non-respirable particles) comprised of the active compound, which the subject inhales through the nose. The respirable or non-respirable particles may be liquid or solid. The quantity of active agent included may be an amount sufficient to achieve dissolved concentrations of active agent on the airway surfaces of the subject of from about $10^{-9}$, $10^{-8}$, or $10^{-7}$ to about $10^{-3}$, $10^{-2}$, or $10^{-1}$ Moles/liter, and more preferably from about $10^{-6}$ to about $10^{-4}$ Moles/liter.

In one embodiment of the invention, the particulate active agent composition may contain both a free base of active agent and a pharmaceutically acceptable salt such as benzamil hydrochloride or phenamil hydrochloride to provide both early release of and sustained release of active agent for dissolution into the mucous secretions of the nose. Such a composition serves to provide both early relief to the patient, and sustained relief over time. Sustained relief, by decreasing the number of daily administrations required, is expected to increase patient compliance with a course of active agent treatments.

Solid or liquid particulate active agent prepared for practicing the present invention should as noted above include particles of respirable or non-respirable size: that is, for respirable particles, particles of a size sufficiently small to pass through the mouth and larynx upon inhalation and into the bronchi and alveoli of the lungs, and for nonrespirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10–500 μm may be used to ensure retention in the nasal cavity.

The dosage of active compound will vary depending on the condition being treated and the state of the subject, but generally may be an amount sufficient to achieve dissolved concentrations of active compound on the nasal airway surfaces of the subject of from about $10^{-9}$, $10^{-8}$, or $10^{-7}$ to about $10^{-3}$, $10^{-2}$, or $10^{-1}$ Moles/liter, and more preferably from about $10^{-6}$ to about $3 \times 10^{-4}$ Moles/liter. Depending upon the solubility of the particular formulation of active compound administered, the daily dose may be divided among one or several unit dose administrations. The daily dose by weight may range from about 0.1, 0.5 or 1 to 10 or 20 milligrams of active agent particles for a human subject, depending upon the age and condition of the subject. A currently preferred unit dose is about 0.005 milligrams of active agent given at a regimen of four administrations per day. The dosage may be provided as a prepackaged unit by any suitable means (e.g., encapsulating in a gelatin capsule).

Pharmaceutical formulations suitable for airway administration include formulations of solutions, emulsions, suspensions and extracts. See generally, J. Naim, Solutions, Emulsions, Suspensions and Extracts, in *Remington: The Science and Practice of Pharmacy*, chap. 86 ($19^{th}$ ed 1995). Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki; the disclosures of which are incorporated by reference herein in their entirety.

In the manufacture of a formulation according to the invention, active agents or the physiologically acceptable salts or free bases thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a capsule, which may contain from 0.5% to 99% by weight of the active compound. One or more active compounds may be incorporated in the formulations of the invention, which formulations may be prepared by any of the well-known techniques of pharmacy consisting essentially of admixing the components.

Mists or aerosols of liquid particles comprising the active compound may be produced by any suitable means, such as by a simple nasal spray with the active agent in an aqueous pharmaceutically acceptable carrier, such as sterile saline solution or sterile water. Administration may be with a pressure-driven aerosol nebulizer or an ultrasonic nebulizer. See, e.g., U.S. Pat. Nos. 4,501,729 and 5,656,256. Suitable formulations for use in a nasal droplet or spray bottle or in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Mists or aerosols of solid particles comprising the active compound may likewise be produced with any solid particulate medicament aerosol generator. Aerosol generators for administering solid particulate medicaments to a subject produce particles which are respirable or non-respirable, as explained above, and generate a volume of mist or aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 or 200 μl to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants (such as oleic acid or sorbitan trioleate), antioxidants and suitable flavoring agents.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formation of an aerosol. A suitable dispersant is lactose, which may be blended with the active agent in any suitable ratio (e.g., a 1 to 1 ratio by weight).

7. Covalent Conjugate of a Pyrazinoylguanidine Sodium Channel Blocker and a Non-absorbable Carrier Moiety In addition to the foregoing, the pyrazinoylguanidine sodium channel blockers described above can be conjugated to a non-absorbable carrier moiety as described above to provide compounds that are active in hydrating mucosal surfaces. Some of these compounds have the formula:

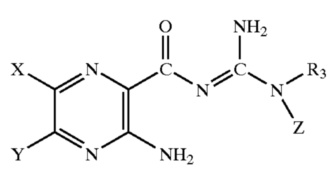

wherein: X, Y, $R_2$ and $R_3$ are as defined above, and Z is a non-absorbable carrier moiety as described above covalently linked to the adjacent nitrogen atom; or a pharmaceutically acceptable salt thereof. Such compounds can be prepared, formulated and administered in essentially the same manner as described above for the same uses as described above.

The following Examples are provided to illustrate the present invention, and should not be construed as limiting thereof. In these Examples, Proton NMR spectra (360 MHz) and carbon NMR spectra (90 MHz) were obtained on a Bruker WM-360 spectrometer using tetramethylsilane as an internal standard. Liquid chromatography (LC)/mass spectroscopy (MS) was performed on a Perkin Elmer Sciex API 100 by one of the following methods:

Method A:YMC Pro C8 column, 5μ, 150×4.6 mm; Mobile phase A=water +0.4% acetic acid, B=acetonitrile (MeCN)+0.4% acetic acid; Gradient: 5% B for 1 min, to 80% B in 7 min. followed by 100% B for 5 min.

Method B: YMC Pro C8 column, 5μ, 150×4.6 mm; Mobile Phase A=water +0.4% acetic acid, B=MeCN+ 0.4% acetic acid; Gradient: 5% B for 1 min, going up to 80% B in 5 min.

Method C: Luna C8 (2)column, 150×4.6 mm, 5 μ, detector λ=360 nm, mobile phase A=water+0.4% acetic acid, B=MeCN +0.4% acetic acid; Gradient: 5% B for 1 min, to 80% B in 7 min, followed by washout with 100% B for 5 min.

Analytical HPLC was performed on a Shimadzu HPLC 10Avp by one of the following methods:

Method D: Luna C18(2) column, 5μ, 250×4.6 mm; detector λ=360 nm; Gradient: A=water +0.1% trifluoroacetic acid(TFA), B=MeCN +0.1% TEA, concentration of MeCN increases from 10 to 60% during a 0–11 min interval, then 60–100% from 11–12 min.

Method E:Symmetry C8 column, 150×4.6 mm; detector λ=360 nm; Gradient:A=water+0.1% TFA, b=MeCN +0.1% TFA, concentration of B increases in the A/B mixture from 10 to 60% during the 0–11 min interval, then B increases to 60–100% from 11–12 min.

Preparative HPLC was performed on a Gilson CombiChem by methods described in below in the Examples.

EXAMPLE 1

Synthesis of Dimeric Compounds

Referring to Scheme 1, dimer compounds of Formula I have been synthesized as shown in TABLE 1. The synthesis begins with 1-(3,5-diamino-6-chloropyrazinoyl)-2-methyl-2-thiopseudourea hydroiodide (intermediate II, prepared as described in U.S. Pat. No. 4,246,406 to Cragoe et al) . . . Intermediate II was treated with N-(benzyloxycarbonyloxy) succinimide and triethylamine in N,N-dimethylformamide (DMF) to give the carbobenzyloxy(Cbz)-protected intermediate III. Formation of the Cbz-protected dimer V occurs upon treatment of intermediate III with the appropriate diamine IV in the presence of mercury(II) chloride and triethylamine in DMF (conditions reported by W. Su, *Synth. Comm.,* 26, 407–413 (1996) for the preparation of Cbz-protected guanidines). Treatment of dimer intermediate V with hydrobromic acid in acetic acid removes both of the Cbz-protecting groups to give amiloride dimer I as the dihydrobromide salt. The hydrobromide salts of I could be converted to the free base of I by treatment with a strong base like potassium hydroxide in aqueous media. The free base can then be converted to other salt forms (e.g,. hydrochloride salt or other pharmaceutically acceptable salt forms) by treatment with the appropriate acid.

TABLE 1

Dimers

| Compound (AMR code) | Structure | IC50 (nM) | Max Inhibition (%) from baseline | Effect of washout (3) 100% = Baseline |
|---|---|---|---|---|
| CF-509 1363 | [structure] | 1275 | 79 | 77 |
| CF-510 1390 | [structure] | 81 | 73 | 21 |
| CF-511 1438 | [structure] | 114 | 86 | 54 |
| CF-512 1465 | [structure] | 197 | 92 | 60 |
| CF-514 1504A | [structure] | 121 | 96 | 20 |
| CF-515 1504 | [structure] | 133 | 99 | 12 |
| CF-516 1527 | [structure] | 330 | 90 | 65 |
| *CF-519 1604 | [structure] | 1075 | 85 | 100 |

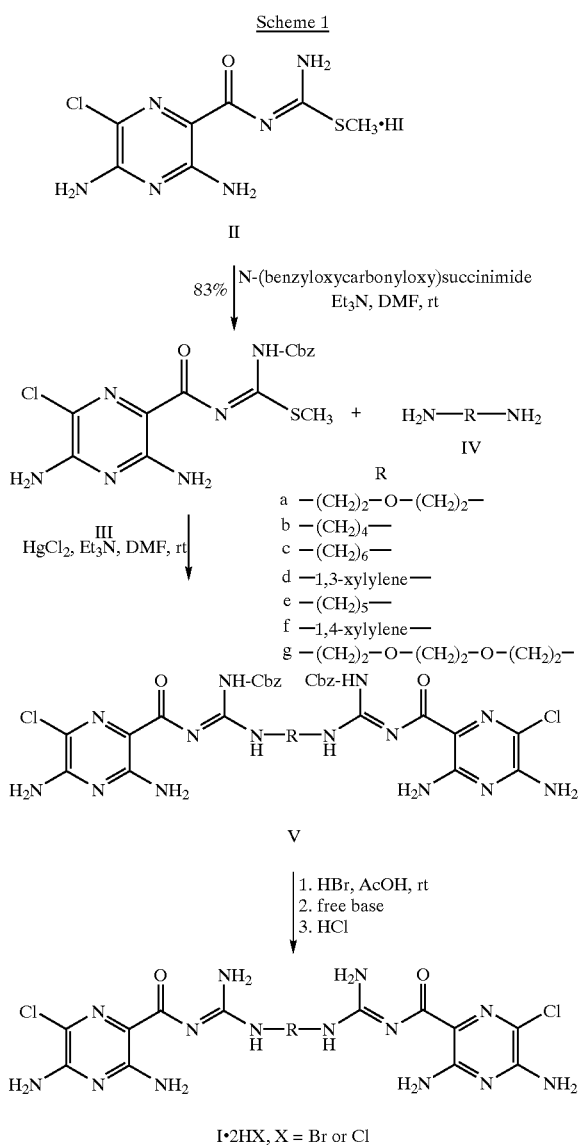

Scheme 1

EXAMPLE 2 THROUGH 10

Preparation of Dimeric Analogues of Amiloride

EXAMPLE 2

N-Cbz-1-(3,5-diamino-6-chloropyrazinoyl)1y)-2-methyl-pseudothiourea (III)

1-(3,5-Diamino-6-chloropyrazinoyl)-2-methyl-pseudothiourea hydroiodide (II, 494 mg, 1.27 mmol) was dissolved in a mixture of anhydrous DMF(10 mL), and triethylamine (3 mL) followed by treatment with N-(benzyloxycarbonyloxy) succinimide (470 mg, 1.7 mmol) dissolved in DMF(3 mL). The reaction mixture was stirred overnight at room temperature. After this time, the reaction mixture was concentrated under reduced pressure and the residue suspended in ethyl acetate (30 mL). Silica gel (25 g) was added to the solution and the solvent was evaporated to leave the silica gel impregnated with the crude product that was purified by flash chromatography on a FlashElute™ system from Elution Solution (P.O. Box 5147, Charlottesville, Va. 22905) using a 90 g silica gel cartridge (eluent:hexanes, ethyl acetate=1:2). The purified N-Cbz-1-(3,5-diamino-6-chloropyrazinoyl)-2-methyl-pseudothiourea (III) was yield);$^1$H NMR (360 MHz, DMSO-d$_6$) δ2.33 (s, 3H), 2.61 (s, 3H), 4.99 (s, 2H), 7.39 (m, 10H), 13.7 (s, 1H); API MS m/z=395 $[C_{15}H_{15}ClN_6O_3S+H]^{30}$; LC/MS (Method A)>99%, $t_r$=10.1 min.

EXAMPLE 3

1,5-Bis[(3,5-diamino-6-chloropyrazinoyl)/guanidino]-3-oxa-pentane Dihydrobromide (Ia)

A solution of 1,5-diamino-3-oxa-pentane (IVa, 30 μL, 0.3 mmol) in dry DMF (100 μL) was added to intermediate III (226 mg, 0.6 mmol) and stirred in anhydrous DMF(10 mL). Triethylamine (480 μL, 3.4 mmol) in DMF (1mL) and mercury(II) chloride (154 mg, 0.6 mmol) in DMF(100 μL) were added and the reaction mixture was stirred overnight at room temperature. The reaction mixture was filtered through silica gel and the filtrate concentrated under reduced pressure. The residue was purified by flash chromatography on FlashElute™ system from Elution Solution using 90 g silica gel cartridge (eluent: ethyl acetate, hexanes =7:1). The fractions were analyzed by LC/MS (Method B) and those fractions containing the desired product were combined and concentrated to give 1,5-bis[(N-Cbz-3,5-diamino-6-chloropyrazinoyl) guanidino]-3-oxa-pentane (Va, 102 mg, 44% yield); LC/MS>99% (Method B); API MS m/z=797 $[C_{32}H_{34}Cl_2N_{14}O_7+H]^+$.

Intermediate Va (50 mg) was dissolved in 30% HBr in acetic acid (10 mL) and the mixture was stirred for 2 d. The volume of the reaction mixture was reduced (to 4 mL) when a precipitate formed. Ethyl ether (10 mL) was added to the acetic acid/product mixture and the precipitate was collected by vacuum filtration, washed with additional ether, dried and then purified by preparative HPLC on Luna column [C18(2), 5μ, 250×21.2 mm; mobile phase MeCN/water containing 0.1% TFA; gradient: 5% MeCN from the 0–2 min interval, increased from 5% –40% MeCN from 2–10 min, 40%–80% MeCN from 10–19 min, 40% -80% MeCN from 19–23 min, 80%–100% MeCN and 100% MeCN from 23–25 min.] Fractions containing the target compound were combined, concentrated under reduced pressure and the residue redissolved in 10% HBr and evaporated to dryness and washed with THF. The product Ia was obtained as a yellow powder: 18.9 mg (41% yield from V); $^1$H NMR (360 MHz, DMF-d$_7$) δ3.80 (m, 4H), 3.88 (m, 4H), 7.51 (br s, 4H), 9.58 (m, 2H), 10.97 (s, 2H). API MS m/z=529 $[C_{16}H_{22}Cl_2N_{14}O_3+H]^{30}$; HPLC (Method D)>99%, $t_r$=6.72 min.

EXAMPLE 4

1,4-Bis [(3,5-diamino-6-chloropyrazinoyl) guanidino]butane dihydrobromide (Ib)

A solution of 1,4-diaminobutane (IVb, 24 mg, 0.3 mmol) in dry DMF (230 μL) was added to III (213 mg, 0.54 mmol) in anhydrous DME(10 mL), followed by addition of triethylamine (480 μL, 3.4 mmol) in DMF (1 mL) and mercury(II), chloride (146 mg, 0.53 mmol) in DMF (600 μL). The reaction mixture was stirred for 3 d at room temperature, then filtered through silica gel. The filtrate was concentrated under reduced pressure and the residue was dissolved in 30% HBr in acetic acid (20 mL) and stirred overnight at rt. The reaction mixture was poured into ethyl ether (150 mL) resulting in the formation of a precipitate that was isolated by vacuum filtration and washed with water (3×0.5 mL). The solid precipitate was purified by preparative HPLC on a Luna C18(2) column [5 μ, 250×21.2 mm; flow rate =20 mL/min; mobile phase consists of MeCN/water containing 0.1% TFA; gradient: 10% MeCN from the 0–2 min interval, concentration of MeCN increased from 10% -40% from 2–10 min, 40% - 100% MeCN from 10-19 min, 100% MeCN from 19–23 min, MeCN decreased from 100% –10% from 23–25 min]. Fractions containing the target compound were combined and concentrated under reduced pressure to give a residue that was redissolved in 10% HBr and evaporated to dryness and washed with ethyl ether to give Ib as a pale yellow solid: 19.4 mg (10.1% yield); $^1$H NMR (360 MHz, DMSO-d$_6$) δ1.62 (br s, 4H), 7.43 (s, 4H), 8.77 (br s, 2H), 8.89 (br s, 2H), 9.24 2H), 10.48 (s, 2H); $^{13}$C NMR (90 MHz, DMSO-d$_6$) δ24.8, 40.4, 108.9, 119.5, 153.1, 154.2, 155.9 and 165.1; API MS=513 $[C_{16}H_{22}Cl_2N_{14}O_2+H]^{30}$; HPLC (Method D) >99%, $t_r$ 6.26 min.

EXAMPLE 5

1,5-Bis [(3,5-diamino-6-chloropyrazinoyl) guanidino]hexane Dihydrobromide (Ic)

Compound Ic was prepared following the same procedure described for Ib. The Cbz-protected pseudothiourea III (226 mg, 0.6 mmol) and 1,6-diaminohexane (IVc, 34.9 mg, 0.3 mmol) reacted in the presence of trietliylamine (480 μL, 3.4 mmol) and mercury(II) chloride (162.9 mg, 0.6 mmol) to give the crude intermediate Vc, which was treated with 30% HBr in acetic acid as previously described. The crude product was purified by preparative HPLC on a Luna C 18(2) column [5μ, 250×21.2 mm; flow rate=20 mL/min; mobile phase: MeCN/water (containing 0.1 % TFA); gradient: 15% MeCN for 0–2 min interval, increase concentration of MeCN from 15% –30% from 2–10 min, 30% –50% MeCN from 10–19 min, 50% –100% MeCN from 19–23 min, then decrease concentration MeCN from 100% –15% from 23–25 min]. Fractions containing the target compound were combined and concentrated under reduced pressure to give a residue that was redissolved in 10% HBr and evaporated to dryness and washed with ethyl ether to give Ic: 28.8 mg (13.5% yield based on III);$^1$H NMR(360 MHz, DMSO-d$_6$,) δ1.38 (br s, 4H), 1.59 (br s, 4H), 3.38 (m, 2H), 7.44 (s, 4H), 8.75 (br s, 2H), 8.90 (br s, 2H), 9.19 (s, 2H) and 10.47 (s, $^{13}$C NMR (90 MHz, DMSO-d$_6$,) δ25.5, 27.5, 40.9, 108.9, 119.6, 153.1, 154.2, 155.8 and 165.1; API MS m/z=541 $[C_{18}H_{26}Cl_2N_{14}O_2+H]^{30}$; HPLC (Method D) 95.2%, $t_r$=7.26 min.

EXAMPLE 6

1. 3-Bis [(35-diamino-6-chloropyrazinoyl) guanidino]xylylene Dihydrobromide (Id)

Compound Id was prepared following the same procedure described for Ib. Triethylamine (480 μL, 3.4 mmol) and mercury(II) chloride (192 mg, 0.7 mmol) were added to a solution of Cbz-protected pseudothiourea III (280 mg, 0.7 mmol) and 1,3-xylylene diamine (IVd, 50 mg, 0.3 mmol) in DMF (30 mL). The reaction mixture was stirred at rt for 48 h and worked up the same as in the procedure for Ib and followed by treatment of the crude intermediate Vd with 30% HBr in acetic acid as previously described. The resulting crude product (yellow solid) was crystallized from methanol and further purified by preparative HPLC on a symmetry C8 column [7μ, 200×40 mm; flow rate=40 mL/min; mobile phase: MeCN/water (containing 0.1% TFA); gradient:concentration of MeCN 5% for 0–2 min interval, then increased from 5% –20% MeCN from 2–10 min, 20% –60% MeCN from 10–30 min, 60% –100% MeCN from 30–33 min and concentration decreased from 100% –5% MeCN from 33–35 min]. Product isolation and further treatment with HBr as previously described gave the product Id as pale yellow solid: 31.2 mg (12.1% yield from III); $^1$H NMR (360 MHz, DMSO-d$_6$,) δ4.60 (d, J=5.2 Hz, 4H), 7.40–7.42 (m, 7 h), 9.03 s, 4H), 9.61 (s, 2H) and 10.59 (s, 2H); API MS m/z=561 $[C_{20}H_{22}Cl_2N_{14}O_2+H]^+$; HPLC (Method E) 97.3%, $t_r$ =5.5 min.

EXAMPLE 7

1,5-Bis[(3,5-diamino-6-chloropyrazinoyl)guanidino] pentane Dihydrobromide (Ie)

Compound Ie was prepared following the same procedure described for Ib. The Cbz-protected pseudothiourea III (280 mg, 0.7 mmol) and 1,5-diaminopentane (IVe, 37 mg, 0.35 mmol) were reacted in the presence of triethylarnine (480 μL, 3.4 mmol) and mercury(GI) chloride (192 mg, 0.7 mmol). The reaction mixture was stirred at rt for 24 h and worked up the same as in the procedure for Ib and the resulting crude intermediate Ve was treated with 30% HBr in acetic acid for 24 h as previously described. The reaction mixture was poured into ethyl ether (200 mL), the precipitate was collected by filtration, washed with ether, THF and then crystallized twice from 12% HBr to give crude Ie (117 mg, 87% purity, 47% yield from III) as a yellow solid. A portion of this material (78 mg) was crystallized again from 12% HBr to give Ie as a pale yellow solid: 32 mg (12.8% yield from III);$^1$H NMR (360 MHz, DMSO-d$_6$) δ1.39 (m, 2H), 1.61 (m, 4H), 3.31 (m, 4H), 7.44 (br s, 4H), 8.72 (br 2H), 8.90 (br s, 2H), 9.20 (s, 2H) and 10.49 (s,2H); $^{13}$C NMR(90 MHz, DMSO-d$_6$) δ23.1,27.3, 40.8,109.0, 119.7, 153.1, 154.2,155.9 and 165.2; API MS m/z=527 $[C_{17}H_{24}Cl_2N_{14}O_2+H]^{30}$; HPLC (Method E) 95.3%, $t_r$ 32 5.72 min.

EXAMPLE 8

1,5-Bis[(3,5-diamino-6-chloropyrazinoyl) ganidino] pentane Dihydrochloride (Ie ·X·2 HCl)

The combined mother liquors from the crystallization of Ie were treated with powder KOH until the solution reached pH=11. The precipitate that formed was collected by vacuum filtration, washed with water, and recrystallized twice from 10% aqueous HCl to give Ie 2HCl as a pale yellow solid:27.3 mg (13% yield from III);$^1$H NMR (360 MHz, DMSO-d$_6$) δ1.40 (m, 2H), 1.61 (m, 4H), 3.34 (m, 4H), 7.41 (br s, 4H), 8.80 (br s, 2H), 8.93 (br s, 2H), 9.29 (s, 2H) and 10.52 (s, 2H); $^{13}$C (90 MHz DMSO-d$_6$) δ23.1, 27.3, 40.8, 109.0, 119.7, 153.2, 154.2, 155.9 and 165.2; API MS m/z=527 $[Cl_7H_{24}Cl_2N_{14}O_2+H]^{30}$; HPLC (Method E) 95.2%, $t_r$=5.

EXAMPLE 9

1,4-Bis [(3,5-diamino-6-chloropyrazinoyl) guanidino]xylylene Dihydrobromide (If)

Compound If was prepared following the same procedure described for Ib. The Cbz-protected pseudothiourea III (280 mg, 0.7 mmol) and 1,4-xylylenediamine (IVf, 50 mg, 0.30 mmol) were reacted in the presence of triethylamine (480 μL, 3.4 mmol) and mercury(II) chloride (192 mg, 0.7 mmol). The reaction mixture was stirred at rt for 4 d and then it was filtered through silica gel and concentrated under reduced pressure. The residue was suspended in anhydrous DMF (10 mL) and treated with tetrabutylammonium borohydride (50 mg, 0.17 mmol) in DMF (1 mL) and stirred for 15 min at rt to get rid of residual mercury(II) chloride. The reaction mixture was filtered through silica gel and concentrated to give a residue (Vf) that was treated with 30% HBr in acetic acid (20 mL) for 7 d at rt and 1 d at 45 °C. The reaction mixture was poured into ether (200 mL) and the solid that precipitated was collected by filtration, washed with ether, THF and crystallized twice from methanol to give a pale yellow solid: 74 mg (31% yield from III); $^1$H NMR (360 MHz, DMSO-$d_6$) δ4.60 (d, J=4.3 Hz, 4H), 7.45 (s, 4H), 8.91 (br s, 2H), 8.99 (br s, 2H 2H) and 10.56 (s, 2H); $^{13}$C NMR(90 MHz, DMSO-$d_6$) δ44.1, 109.1, 119.7, 128.1, 135.4, 153.3, 154.3, 156.0 and 165.3; API MS m/z=561 $[C_{20}H_{22}Cl_2N_{14}O_2+H]^{30}$; HPLC (Method E) 95.7%, $t_r$ =6.31 min.

EXAMPLE 10

1,8-Bis[(3,5-diamino-6-chloropyrazinoyl) guanidino]-3,6-dioxa-octane Dihydrochloride (Ig)

A solution of 2,2'-(ethylenedioxy)bis(ethylamine) (IVg, 45 mg, 0.3 mmol) in dry DMF (100 μL was added to III (240 mg, 0.7 mmol) in dry DMF (30 mL), followed by addition of triethylamine (480 μL, 3.4 mmol) in DMF (1 mL) and mercury(I) chloride (165 mg, 0.6 mmol) in DMF (600 μL). The reaction mixture was stirred 16 h at room temperature, then additional III (20 mg) was added and reaction mixture was stirred an additional 8 h at 40 °C. The reaction mixture was cooled to room temperature and treated with tetrabutylammonium borohydride (50 mg, 0.17 mmol) in DMF (1 mL) with stirring for 15 min at room temperature. The reaction mixture was filtered through silica gel, concentrated under reduced pressure to give a solid residue. This was dissolved in 30% HBr in acetic acid (20 mL) and stirred for 8 h at 40 °C, then poured into ether (200 mL). The resulting precipitate was collected by filtration and washed with ether. The solid was dissolved in water (25 mL), the solution filtered, and the filtrate concentrated under reduced pressure. The resulting residue was dissolved again in minimal 10% HBr and powdered NaOH is added to pH=11. A precipitate formed and was collected by filtration, washed with water and dried to give the free base (98 mg, 56% yield). A portion of this material (58 mg) was dissolved in 10% HCl and then concentrated under reduced pressure. The residue is washed with ether and dried to give Ig as a pale yellow solid: 64 mg (32% yield from III);$^1$H NMR (360 MHz, DMSO-$d_6$) δ 3.56 (br s, 4H), 3.63 (br s, 8H), 7.4 (br s, 4H), 9.09 (br s, 4H), 9.52 (br s, 2H) and 10.70 (s, 2H); $^{13}$C NMR ( MHz, DMSO-$d_6$) δ41.1, 67.7, 69.5, 108.9, 119.7, 153.3, 154.2, 155.8 and 165.3; API MS m/z =573 $[C_{18}H_{26}Cl_2N_{14}O_4 +H]^{30}$; LC (Method C) 97.6%, $t_r$=4.2

EXAMPLE 11

Potency of Dimeric Compounds

Two pharmacologic assays were used to determine the relative potency of the dimers described herein. The first assay examined the expression of the subunits α, β, and γ of recombinant apical membrane epithelial Na$^+$ channel (or "rENaC") in Xenopus oocyte, as follows: cRNAs for all three ENaC subunits were injected into oocytes via conventional microinjection techniques. After two to three days, two electrode voltage clamp protocols were used to measure ENaC-mediated Na$^+$currents. Test compounds were assayed using cumulative drug addition protocols known in the art. Single oocytes were used for single compounds. Compounds tested were then compared to dose-effect relationships for amiloride and benzamil in the same batch of injected eggs.

In the second potency assay, airway epithelial monolayers mounted were in Using chambers:The principal assay consisted of tests of lumenal drug inhibition of airway epithelial Na$^+$ currents. Cells obtained from freshly excised human or dog airways were seeded onto SNAP-well Inserts (CoStar), cultured under air-liquid (ALI) conditions in hormonally defined media. The cells were assayed for Na$^+$ transport activity while bathed in Krebs bicarbonate Ringer (KBR) in the Ussing chambers under voltage clamp conditions. All test drug additions were to the mucosal bath with half-log dose addition protocols ($10^{-11}$M–$10^{-5}$ M). All drugs were made in standard stocks of $10^{-2}$ M drug in DMSO. Eight preparations were typically run in parallel; two preparations/ run were routinely used to assay amiloride and benzamil. After the maximal concentration ($10^{-4}$ M) was administered, the lumenal bath was exchanged three times with fresh KBR solution, which was defined as the "washout" effect. All data from the voltage clamps were collected via a computer interface and analyzed off-line.

Dose-effect relationships for all compounds were considered and analyzed by the Prism 3.0 program. The IC$_{50}$, maximal effective concentrations, and percent washout were calculated and compared to those of amiloride and benzamil as reference compounds.

EXAMPLE 12

Absorption Assays

Compounds useful in the present invention preferably have the characteristics of high potency and non- or decreased absorbability into mucosal surfaces. Two pharmacologic assays were employed to test the absorption of compounds illustrated in TABLE 1.

The first assay is referred to an assay of reversibility. Empirically, the percent of wash-out correlates with cellular uptake. The relationship is complex because reversibility is also a function of potency. However, reversibility is a quick and simple screen. An example of the information obtained by such as assay is shown in FIG. 1. The compounds that "reverse" best in this assay referenced to benzamil were also the least absorbed in the confocal assay, as described below.

Figure 2:
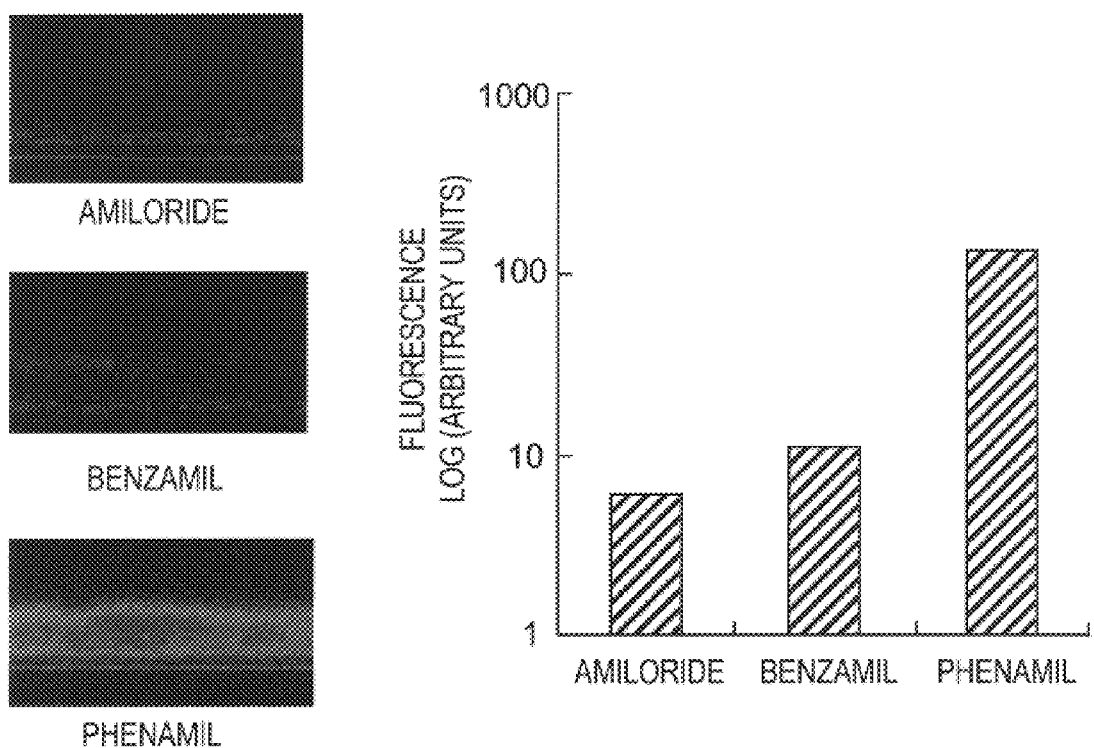
FIG. 2 is an example of a confocal microscopy assay of drug uptake into cultured airway epithelia. In this assay, a compound ($10^{-4}$ M) is placed on the airway surface and fluorescence from the cells collected by x-z scanning confocal microscopy. The images shown on the left depict fluorescence in the cells 20 minutes after exposure to amiloride, benzamil and phenmnil. Quantitation of the drug uptake is graphically illustrated on the right in terms of units of fluorescence.

The second assay utilizes confocal microscopy of amiloride congener uptake: Virtually all amiloride-like molecules fluoresce in UV range. This property of these molecules was used to directly measure cellular uptake, using a x-z confocal microscope (Leica). As an example of the results obtained by this assay are shown in FIG. 2. In the experiment shown in FIG. 2, equimolar concentrations of amiloride and compounds of rapid (benzamil) and very rapid uptake (phenamil) were placed on the apical surface of airway cultures on the stage of the confocal microscope. Serial x-z images were obtained with time and the magnitude of fluorescence accumulating in the cell compartment quantitated and plotted. The assay was subsequently optimized to test for compounds that absorbed into cells less rapidly than amiloride. Two compounds from the synthesis series described above (CF-509 and CF-519) appear to fulfil this criterion. Compounds that were equipotent or greater with amiloride were tested for wash-out as described above. However, because wash-out may reflect both potency and cell uptake, the rate of accumulation of fluorescence (indexed to the specific fluorescence/emission spectrum of each compound) in the cell compartment as a function of time was also routinely measured. The relative cellular uptake of each test compound was then compared to the reference compounds (amiloride, benzamil) as for potency assays.

The foregoing is illustrative of the present invention, and is not to be construed as limiting thereof. The invention is defined by the following claims, with equivalents of the claims to be included therein.

That which is claimed is:

1. A pharmaceutical formulation in a pharmaceutically acceptable carrier solution, comprising the compound of the formula $P_1$-L-$P_2$, wherein:

$P_1$ is a pyrazinoylguanidine sodium channel blocker;

L is a linking group; and $P_2$ is selected from the group consisting of pyrazinoylguanidine sodium channel blockers and $P2Y_2$ receptor agonists;

or a pharmaceutically acceptable salt thereof.

2. The pharmaceutical formulation according to claim 1, wherein $P_2$ is a pyrazinoylguanidine sodium channel blocker.

3. The pharmaceutical formulation according to claim 1, wherein: $P_1$ and $P_2$ are each independently selected from the group consisting of compounds of the formula:

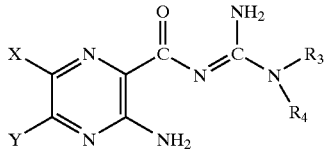

wherein:

X is selected from the group consisting of chloro, bromo, iodo, loweralkyl, lower-cycloalkyl having from 3 to 7 carbons, phenyl, chlorophenyl, bromophenyl, Z-thio and Z-sulfonyl wherein Z is selected from the group consisting of loweralkyl, oxyalkyl, and phenyl-loweralkyl;

Y is selected from the group consisting of hydroxyl, mercapto, loweralkyloxy, loweralkylthio, chloro, loweralkyl, lowercycloalkyl having from 3 to 6 carbons, phenyl, and amino having the structure:

wherein:

R is selected from the group consisting of hydrogen, amino, amidino, lower-cycloalkyl having 3 to 6 carbon atoms, loweralkyl, hydroxyloweralkyl, haloloweralkyl, lower-(cycloalkylalkyl) having 3 to 6 carbons in the ring, phenyl-loweralkyl, lower-(alkylaminoalkyl), lower-alkenyl, phenyl, halophenyl, and lower-alkylphenyl;

$R_1$ is selected from the group consisting of hydrogen, loweralkyl, loweralkenyl, and additionally;

R and $R_1$ can be joined to form a lower alkylene;

$R_2$ is selected from the group consisting of hydrogen and loweralkyl;

$R_3$ and $R_4$ are independently selected from the group consisting of hydrogen, loweralkyl, hydroxy-loweralkyl, phenyl-loweralkyl, (halophenyl)-loweralkyl, lower-(alkylphenylalkyl), (loweralkoxyphenyl)-loweralkyl, naphthyl-loweralkyl, (octahydro-1-(azocinyl)-loweralkyl, pyridyl-loweralkyl, and loweralkyl radicals linked to produce with the nitrogen atom to which they are attached a 1-pyrrolidinyl, piperidino, morpholino, and a 4-loweralkyl-piperazinyl group, and phenyl; and L is selected from the group consisting of loweralkyl, hydroxy-loweralkyl, phenyl-loweralkyl, (halophenyl)-loweralkyl, lower-(alkylphenylalkyl), (loweralkoxyphenyl)-loweralkyl, naphthyl-loweralkyl, (octahydro-1-azocinyl)-loweralkyl, pyridyl-loweralkyl, and loweralkyl radicals linked to produce with the nitrogen atom to which they are attached a 1-pyrrolidinyl, piperidino, morpholino, and a 4-loweralkyl-piperazinyl group, and phenyl.

4. The pharmaceutical formulation according to claim 1, wherein $P_2$ is a nucleotide or dinucleotide $P_2Y_2$ receptor agonist.

5. The pharmaceutical formulation according to claim 1, wherein $P_2$ is a dinucleotide having the formula:

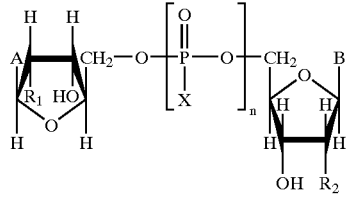

wherein:

A and B are each independently a purine or pyrimidine base;

$R_1$ and $R_2$ are each independently selected from the group consisting of H or OH;

X is OH, SH, O or S; and n is from 1 to 6;

with said dinucleotide covalently joined to L by covalent attachment to A or B or covalent attachment to the ribose or deoxyribose ring to which A and B are joined.

6. The pharmaceutical formulation according to claim 1, wherein the compound has the structure:

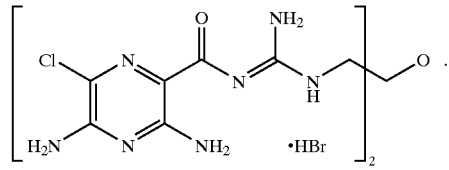

7. The pharmaceutical formulation according to claim 1, wherein the compound has the structure:

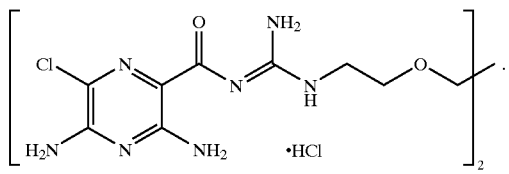

8. The pharmaceutical formulation according to claim 1, wherein $P_1$ is selected from the group consisting of amiloride, benzamil and phenamil.

9. The pharmaceutical formulation according to claim 1, wherein the pharmaceutical formulation is useful for treating a mucosal surface in a subject in need thereof.

10. The pharmaceutical formulation according to claim 9, wherein the mucosal surface is an airway mucosal surface.

11. The pharmaceutical formulation according to claim 9, wherein the mucosal surface is a gastrointestinal mucosal surface.

12. The pharmaceutical formulation according to claim 9, wherein the subject is a human or animal subject.

13. The pharmaceutical formulation according to claim 9, further comprising at least one other compound useful in the treatment of a mucosal surface in a subject in need thereof.

14. The pharmaceutical formulation according to claim 1, wherein the pharmaceutical formulation is suitable for administration to a subject in thereof.

15. The pharmaceutical formulation according to claim 14, wherein the pharmaceutical formulation is suitable for topical administration.

16. The pharmaceutical formulation according to claim 14, wherein the pharmaceutical formulation is suitable for oral administration.

17. The pharmaceutical formulation according to claim 14, wherein the pharmaceutical formulation is suitable for rectal administration.

18. The pharmaceutical formulation according to claim 14, wherein the pharmaceutical formulation is suitable for inhalational administration.

19. The pharmaceutical formulation according to claim 14, wherein the pharmaceutical formulation is suitable for transdermal administration.

20. The pharmaceutical formulation according to claim 14, wherein the pharmaceutical formulation is suitable for parenteral administration.

* * * * *

UNITED STATES PATENT AND TRADEMARK OFFICE
CERTIFICATE OF CORRECTION

PATENT NO.     : 6,613,345 B2
DATED          : September 2, 2003
INVENTOR(S)    : Boucher, Jr.

It is certified that error appears in the above-identified patent and that said Letters Patent is hereby corrected as shown below:

Column 26,
Line 56, should read -- 95.2 %, $t_r$ = 5.78 min. --

Column 27,
Line 54, should read -- (Method C) 97.6%, $t_r$ = 4.23. --

Column 29,
Line 30, should read -- 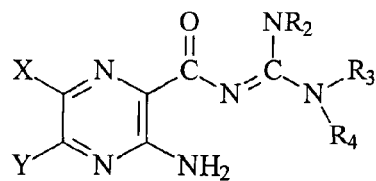 --

Signed and Sealed this

Twenty-fourth Day of August, 2004

JON W. DUDAS
*Director of the United States Patent and Trademark Office*